United States Patent [19]

Wideman

[11] Patent Number: 4,628,140
[45] Date of Patent: Dec. 9, 1986

[54] PROCESS FOR THE PRODUCTION OF DIENES FROM ALDEHYDES

[75] Inventor: Lawson G. Wideman, Tallmadge, Ohio

[73] Assignee: The Goodyear Tire & Rubber Company, Akron, Ohio

[21] Appl. No.: 835,494

[22] Filed: Mar. 3, 1986

[51] Int. Cl.⁴ .......................... C07C 1/24; C07C 1/253
[52] U.S. Cl. ...................................... 585/606; 585/603
[58] Field of Search ................ 585/606, 603, 607, 608

[56] References Cited

U.S. PATENT DOCUMENTS

| | | | |
|---|---|---|---|
| 4,524,233 | 6/1985 | Hsu et al. | 585/606 |
| 4,547,614 | 10/1985 | Vavere | 585/606 |
| 4,560,822 | 12/1985 | Hoelderich et al. | 585/606 |
| 4,587,372 | 5/1986 | Hsu | 585/606 |

*Primary Examiner*—Asok Pal
*Attorney, Agent, or Firm*—D. O. Nickey

[57] ABSTRACT

This invention is directed to an improved process for the conversion of an aldehyde to a diolefin comprising contacting an aldehyde of 4 to 6 carbon atoms in the vapor phase at a temperature of 250° to 400° C. with a catalyst, the improvement comprising the addition of from 0.10 to 5 percent by weight of an aromatic compound to the aldehyde feed. Representative of the aromatic compounds useful in the instant invention are: phenol, catechol, alkylated catechol, resorcinol, hydroquinone and aniline; wherein the alkyl radical can be from 1 to 10 carbon atoms.

11 Claims, No Drawings

PROCESS FOR THE PRODUCTION OF DIENES FROM ALDEHYDES

TECHNICAL FIELD

This invention relates to a process for converting aldehydes to dienes. More specifically, this invention is concerned with an additive to the aldehyde feed which will decrease the rate of deactivation of the catalyst.

BACKGROUND ART

Dienes, especially isoprene, are useful as monomers for the manufacture of synthetic rubbers. Several fundamental processes have been used to construct the isoprene $C_5$ skeleton from smaller carbon units. These processes are not commercially accepted in that there are numerous problems associated with each particular synthesis route.

European Patent Application No. 80,449 discloses the synthesis of isoprene from linear butenes wherein mixed linear butenes are catalytically isomerized to a mixture of cis and trans-butene-2 and then hydroformylating the butene-2 mixture to 2-methylbutanal (2MBA) in the presence of a homogeneous rhodium catalyst and an organic ligand. The 2MBA is then dehydrated to isoprene in the presence of an acidic heterogeneous catalyst at elevated temperatures. The preferred catalyst for the dehydration step is a boron phosphate catalyst which is described in British Patent No. 1,385,348. The dehydration reaction is endothermic, and under preferred conditions, the reaction is performed in the vapor phase over a fixed bed of catalyst at elevated temperatures from about 200 to about 400° C. This reference does not disclose the length of time the catalyst performs at such selectivities and conversions (lifetime). Commercial production of isoprene via the aldehyde dehydration route has not been established since the dehydration catalyst is known to have short lifetimes which limit its utility in commercial applications.

U.K. Patent No. 1,385,348 relates to the conversion of aldehydes to dienes with conjugated double bonds. This British patent discloses that the preferred acid dehydration catalysts are mixed acid anhydrides, for example, boron phosphate, silica borate or silica titanate. There is no disclosure in the U.K. patent regarding the duration of conversions and selectivities and/or the number of regenerations required during any particular time period.

U.K. Patent No. 2,093,060 relates to the preparation of dienes, especially isoprene, from a corresponding carbonyl compound in which magnesium ammonium phosphate or its decomposition products are used as the dehydration catalysts.

U.S. Pat. No. 4,524,233 discloses an improved boron phosphate catalyst wherein the catalyst is prepared by combining phosphoric acid and boric acid at such molar ratios that the ratio of P/B is less than 1 but more than 0.6. The boron phosphate is then contacted with from 0 to 10 mole percent based on moles of boron with ammonia or an amine. The thus treated boron phosphate is then calcined in air and steamed prior to its use. U.S. Pat. No. 4,524,233 also suggests that the 2MBA feed to the dehydration reactor may be diluted with a solvent such as pentane, hexane, heptane, octane and nonane to lessen the deactivation of the catalyst in the dehydration reaction. U.S. Pat. No. 4,524,233 also suggests that the boron phosphate catalysts have incorporated therein from 0.1 to 10 weight percent graphite to further lessen the deactivation of the catalyst.

A disadvantage associated with known catalysts to dehydrate aldehydes is that catalyst life depends on many factors which include catalyst composition, structure, activity, operating temperatures, and coke deposition. Coke deposition is understood to denote coke (carbonaceous) deposits formed on the catalyst during the dehydration reaction.

The use of boron phosphate as a catalyst for the dehydration of alcohols such as 2-butanol and 2-methyl-2-butanol is known. See Jewur and Moffat, *Journal of Catalysis*, 57, 167–176 (1979). The problems associated with an aldehyde dehydration are different and more difficult to overcome than those found in alcohol dehydrations. For example, the boron phosphate dehydration of 2-methylbutanol yields only 2-methyl-2-butene and 2-methyl-1-butene, while dehydration of 2MBA yields primarily methylisopropyl ketone, 2-methyl-2-butene, 2-methyl-1-butene and isoprene. It is the production of the conjugated diolefin, isoprene, that makes the aldehyde dehydration so difficult, since this highly reactive monomer is known to form dimers and/or polymerize in the presence of acid catalysts.

In addition, aldehydes such as 2MBA are known to undergo aldol condensation. This is a reaction between two molecules of an aliphatic aldehyde whereby a 3-hydroxyaldehyde is formed. Dehydration of a 3-hydroxyaldehyde results in the formation of terpenes, a highly undesirable by product that can coke and deactivate the catalyst. Due to these and other differences, catalysts and processes suitable for long term dehydration of alcohols have not been found acceptable for aldehyde dehydrations.

One aspect of this invention is directed to the use of an additive to the aldehyde feed. The instant invention has utility with any catalyst known to promote the dehydration of an aldehyde to a diolefin. The prior art does not suggest, disclose or appreciate that the presence of a specific aromatic compound in the aldehyde feed will unexpectedly lengthen the viable lifetime of the catalyst. In addition, it has been found that the benefits of the instant invention will continue even after the addition of the aromatic compound to the aldehyde feed has ceased, thus allowing for intermittent addition of the aromatic compound to the aldehyde feed.

A portion of the instant invention is thus directed to a process for the catalytic dehydration of an aldehyde to a diene which will allow the catalysts an extended lifetime of high selectivity and low coke deposition. The prior art does not suggest or disclose an additive to the aldehyde feed which would make the dehydration of aldehydes to diene suitable for commercial application.

DISCLOSURE OF THE INVENTION

There is disclosed a process for the conversion of an aldehyde of 4 to 6 carbon atoms to the corresponding diene which comprises contacting the aldehyde in a vapor phase at a temperature of from 200 to 400° C. with a dehydration catalyst, the improvement comprising the addition of from 0.1 to 5.0 percent by weight of an aromatic compound selected from the group consisting of phenol, catechol, alkylated catechol, resorcinol, hydroquinone and aniline; wherein the alkyl radical can be from 1 to 10 carbon atoms; to the aldehyde feed prior to contact with the dehydration catalyst.

There is also disclosed a process for preparing isoprene which comprises passing 2-methylbutanal in the vapor phase over a boron phosphate dehydration catalyst, the improvement comprising the addition of from 0.1 to 5.0 percent by weight of an aromatic compound selected from the group consisting of phenol, catechol, alkylated catechol, resorcinol, hydroquinone and aniline; wherein the alkyl radical can be from 1 to 10 carbon atoms to the 2-methylbutanal prior to contact with the catalyst.

There is further disclosed a process for the dehydration of an aldehyde to the corresponding diene, the improvement characterized in that the aldehyde is in physical admixture with from 0.1 to 5.0 weight percent of an aromatic compound selected from the group consisting of phenol, catechol, alkylated catechol, resorcinol, hydroquinone and aniline; wherein the alkyl radical can be from 1 to 10 carbon atoms.

In addition, there is disclosed a process for the conversion of 2-methylbutanal to isoprene which comprises contacting 2MBA in the vapor phase at a temperature of from 200 to 400° C. with a boron phosphate catalyst, the improvement characterized in that the 2MBA feed contains from 0.1 to 5.0 weight percent of an aromatic compound selected from the group consisting of phenol, catechol, alkylated catechol, resorcinol, hydroquinone and aniline; wherein the alkyl radical can be from 1 to 10 carbon atoms.

Catalysts used to dehydrate an aldehyde to the corresponding diene have consistently shown deactivation with time. This is especially true after the catalyst has been regenerated in an oxidizing atmosphere or steam treated. It has been found unexpectedly that the addition of a specific aromatic compound to the aldehyde feed will slow the rate of deactivation. Through the use of the instant invention, a flat or near level aldehyde conversion with time is observed. Level conversion is highly desirable from a production standpoint in that the effluent from the reactor is of near constant composition. This allows ease of running the reactors and permits a continuous distillation directly from the reactor. Further, the longer the conversion remains level, the less often catalyst regeneration will be required.

It has also been found that dienes with conjugated double bonds can be obtained with advantage from the corresponding aldehydes with the same number of carbon atoms by contacting the aldehyde with a dehydration catalyst wherein the aldehyde contains from 0.1 to 5.0 percent by weight of a specific aromatic compound.

Examples of the aldehydes suitable for use in the process according to the invention include butanal, pentanal, hexanal, 2-methylbutanal, 2,3-dimethylbutanal and 2 or 3-ethylbutanal, 2, 3 or 4 methyl pentanal. 2-methylbutanal is particularly preferred.

The following materials are mentioned as examples of dienes which can be produced by the process according to the invention: 1,3-butadiene, isoprene, 1,3-hexadiene, 2,3 or 4-methyl-1,3-pentadiene, 1,3 pentadiene, 2,3-dimethylbutadiene and 2-ethyl-1,3-butadiene.

The process according to the invention is generally carried out at a temperature from 200° to 400° C. with 275 to 350° C. being preferred.

Representative of the aromatic compounds, which are useful for addition to the aldehyde feed are phenol, catechol, alkylated catechol, resorcinol, hydroquinone and aniline; wherein the alkyl radical can be from 1 to 10 carbon atoms.

Dehydration of aldehydes by the process according to the invention can be carried out in ambient pressure, for example, by vaporizing aldehydes and passing them over the catalysts with or without a carrier gas. Inert gases such as nitrogen, carbon dioxide or hydrocarbons have proven to be of particular advantage. The instant invention can also be carried out under reduced pressure, in which case a reduced pressure of from 0.60 to 1.33 Pa below atmospheric pressure has been found acceptable. Compression pressures of from 2 to 10 bar, more particularly from 2 to 4 bar, can be regarded as both suitable and adequate.

The dehydration catalysts useful in the instant invention are those catalysts known in the art to be useful for the dehydration of aldehydes. More specifically, these dehydration catalysts are usually acid catalysts in that there are active acid sites which are required for the dehydration of the aldehyde. Most preferred are the boron phosphate catalysts, wherein the initial molar ratio of P/B can range from 0.60 to 1.0 which is in admixture with from 1 to 10 weight percent graphite. Initial molar ratio means that the catalyst charged to the reactor or pretreatment vessel has a P/B ratio of less than 1. It has been discovered that during the use of these catalysts, the ratio of P/B approaches but never exceeds 1. It has also been found that the catalysts useful in this invention can be pretreated with steam. For example, a catalyst with an initial P/B ratio of 0.8 is placed in the reactor or a suitable vessel, and ambient pressure steam is passed over the catalyst at an LHSV of at least 2.0, preferably 2.25 for at least $\frac{1}{2}$ hour. By an LHSV of 2.25 is meant 2.25 volumes of liquid water per volume of catalyst is passed through the preheater for vaporization and then over the catalyst.

The catalyst described in U.S. Pat. No. 4,524,233 is specifically preferred herein. Further, the teachings of U.S. Pat. No. 4,524,233 are incorporated herein.

It has been found that dilution of the aldehyde feed to the catalyst with a hydrocarbon such as heptane may be used. This dilution of the aldehyde feed may be in addition to the instant invention which teaches the use of an aromatic compound in the feed to decrease the rate of catalyst deactivation. An advantage of the process of the instant invention is that the catalyst maintains a relatively constant conversion and selectivity, and thus, promotes the commercial feasibility of an aldehyde to diene process.

BEST MODE FOR CARRYING OUT THE INVENTION

A boron phosphate catalyst prepared according to processes known in the art and specifically prepared in accordance with U.S. Pat. No. 4,524,233 was prepared and was steam treated prior to use in the dehydration reactor. Steam treatment can be conducted in a separate vessel or in the reactor. When using the reactor, water is fed to the preheater at a rate of 1.5 to 2.5 volumes liquid water per volume of catalyst per hour and passed over the catalyst at ambient pressure for at least $\frac{1}{2}$ hour and up to 6 hours. Steam is not recommended for use as a diluent for aldehyde dehydrations catalyzed by boron phosphate.

Reactor System

The data reported herein was obtained from a reactor system which was a 1.25 cm by 30 cm Pyrex ™ or quartz tube and a pump system for delivery of the aldehyde. The reactor also contained a 6 cm by 2 cm preheater filled with Pyrex ™ beads. Three thermocouples were present in the reactor, one in the preheater section, one in the first half of the catalyst bed, and one in the lower half of the catalyst bed. The reactor was enclosed with fiberglass heating tape and wrapped additionally with fiberglass tape. Automated temperature controls were used on three separate heaters so that each portion was independently heated and controlled. The reactor was thus run under isothermal conditions.

A pump was used to charge the aldehyde feed continuously into the reactor in a downflow manner with a concurrent nitrogen flow of 14 ml per minute. The effluent from the reactor was passed into a dry ice trap which served as the container for the reaction products. The reactor was run at atmospheric pressure to slightly superatmospheric pressure. The nitrogen gas was used as a protective blanket for the catalyst, feed and effluent system. The nitrogen may also serve as a mild diluent and carrier gas although a nitrogen flow as low as 7 ml/minute changed very little in the reaction system.

The liquid hourly space velocity (LHSV) of aldehyde entering the preheater was set at 2.25 for all reactions. However, the LHSV can be varied. LHSV can be defined by more than one set of conditions. Therefore, as used herein, LHSV is the volume of liquid feed per hour that is passed over the total volume of catalyst. Total volume of catalyst is obtained by pouring the catalyst into a graduated cylinder to a mark of, for example, 40 cc's. The LHSV is simply calculated as follows:

$$LHSV = \frac{90 \text{ cc liquid feed/hour}}{40 \text{ cc catalyst}} = 2.25$$

The effluent (dry ice trap) from the reactor was analyzed with a gas chromatograph having a 4 meter column packed with a suitable material for resolving the components in the reaction mixture. Suitable packing materials, such as TCEP on Chromosorb P, are known to those skilled in analytical chemistry. Other conditions of the gas chromatograph were: detector temperature of 210° C., injection port temperature of 210° C., oven temperature program of 3 minutes at 70° C. followed by a 10.0° C./minute rise to 130° C. Standards were prepared and response factors were determined for isoprene, 2-methyl-2-butene, 2-methyl-1-butene, 2-methylbutanal and methylisopropylketone with undecane as the weighed internal standard.

The aldehyde feed should be as pure as possible; however, minor amounts of other compounds such as the various by-products from the hydroformylation reaction and acids of the aldehyde may be present. To the aldehyde feed is added from 0.1 to 5.0% by weight of an aromatic compound. It is this mixture of the aldehyde and the aromatic compound that is fed to the dehydration reactor.

Experimental—Control

To the reactor as described above was charged a 2MBA feed that did not contain an aromatic compound of this invention. For the control and all the experimentals according to this invention, unless otherwise noted, the LHSV was 2.25, the reactor temperature was 275° C. and the catalyst was boron phosphate with an initial P/B ratio of 0.8 with 2.5% weight graphite which was steam treated prior to use. After a suitable time on stream the % conversion and % selectivities were determined.

The data generated for the control is set out in Table I.

TABLE I

| Hours on Stream | Control - 2MBA % Conversion of 2MBA | % Selectivity to Isoprene |
| --- | --- | --- |
| 2 | 43 | 63 |
| 6 | 32 | 78 |
| 9 | 27 | 82 |
| 12 | 21 | 85 |
| 15 | 20 | 82 |
| 18 | 18 | 82 |
| 21 | 15 | 86 |
| 24 | 12 | 89 |
| 27 | 11 | 87 |
| 30 | 10 | 90 |

From this data it is evident that the ability of the catalyst, without the benefit of this invention, to convert 2MBA to isoprene steadily decreases with time until after about 27 hours the percent conversion is so low that regeneration of the catalyst is required.

Experimental 1

The procedure as set out for the control was used except that for the first 5 hours of the reaction the 2MBA feed contained 1% 4-tertiary butyl catechol. Table II sets out the data collected.

TABLE II

| Hours on Stream | 1% TBC for first 5 hours on Stream | % Conversion of 2MBA | % Selectivity to Isoprene |
| --- | --- | --- | --- |
| 2 | | 30 | 72 |
| 5 | 1% TBC stopped | 13 | 85 |
| 10 | Neat 2MBA | 20 | 89 |
| 15 | | 22 | 82 |
| 20 | | 23 | 81 |
| 25 | | 23 | 81 |
| 30 | | 21 | 81 |
| 35 | | 18 | 81 |
| 40 | | 18 | 80 |
| 45 | | 15 | 83 |
| 50 | | 12 | 82 |

From this data it is evident that 1% of 4-tertiary butyl catechol by weight in the 2MBA feed for only the first 5 hours of the reaction will dramatically decrease the rate of deactivation of the catalyst. Even after an additional 20 hours after the control conversion had decreased to 10% the use of this invention provided for a 12% conversion. It would be evident to a chemical engineer that such an extended period of conversions above 10% would be highly desirable.

Experimental 2

The procedure from Experimental 1 was used except that 1% TBC was placed in the 2MBA feed for the first 3.5 hours and then 0.1% TBC was placed in the feed for the next 18.5 hours and then neat 2MBA was the feed for 18 hours. The results are set out in Table III.

TABLE III

| Hours on Stream | 1% TBC for 3.5 hours - 0.1% TBC for 18.5 hours - Neat 2MBA for 18 hours | % Conversion of 2MBA | % Selectivity to Isoprene |
| --- | --- | --- | --- |
| 2 | | 35 | 70 |
| 3.5 | 1% TBC stopped | 18 | 82 |
| 4 | 0.1% TBC started | 19 | 82 |
| 8 | | 20 | 82 |
| 12 | | 19 | 85 |

TABLE III-continued

1% TBC for 3.5 hours - 0.1% TBC for 18.5 hours - Neat 2MBA for 18 hours

| Hours on Stream | | % Conversion of 2MBA | % Selectivity to Isoprene |
|---|---|---|---|
| 16 | | 18 | 85 |
| 20 | | 17 | 81 |
| 22 | 0.1% TBC stopped | 18 | 80 |
| 24 | Neat 2MBA | 17 | 81 |
| 28 | | 15 | 90 |
| 32 | | 13 | 88 |
| 36 | | 13 | 87 |
| 40 | | 12 | 79 |

From this data it is evident that the use of this invention will enhance the catalyst life.

Experimental 3

The procedure and apparatus as described above was used except that 0.25% TBC by weight was added to the 2MBA feed for the first 2 hours of the reaction the data is set out in Table IV.

TABLE IV 0.25% TBC for 2 hours - neat 2MBA

| Hours on Stream | | % Conversion of 2MBA | % Selectivity to Isoprene |
|---|---|---|---|
| 2 | 0.25% TBC stopped | 33 | 71 |
| 4 | | 33 | 75 |
| 8 | | 31 | 78 |
| 12 | | 30 | 78 |
| 16 | | 28 | 79 |
| 20 | | 25 | 80 |
| 24 | | 22 | 81 |
| 28 | | 20 | 80 |
| 32 | | 18 | 78 |

Experimental 5

The procedure as described above was used except that 0.25% TBC was placed in the 2MBA feed for the first 6 hours and then neat 2MBA was used for 18 hours and then 0.25% TBC was placed in the 2MBA feed for 1 hour and then neat 2MBA was used. The results are set out in Table V.

TABLE V 0.25% TBC for 6 hours, neat 2MBA 18 hours,
0.25% TBC for 1 hour, neat 2MBA 15 hours

| Hours on Stream | | % Conversion of 2MBA | % Selectivity to Isoprene |
|---|---|---|---|
| 2 | | 25 | 80 |
| 4 | | 20 | 83 |
| 6 | 0.25% TBC stopped | 19 | 81 |
| 8 | | 20 | 82 |
| 12 | | 20 | 82 |
| 16 | | 22 | 80 |
| 20 | | 23 | 80 |
| 24 | 0.25% TBC started, 1 hr. | 18 | 83 |
| 28 | Neat 2MBA | 18 | 88 |
| 32 | | 18 | 82 |
| 36 | | 17 | 86 |
| 40 | | 16 | 80 |

From this data it is evident that intermittent and low levels of the aromatic compound in the aldehyde feed will greatly enhance the ability of the catalyst to dehydrate the aldehyde.

Experimental—Control II

The procedure and apparatus as described above was used except that the aldehyde was 2-ethyl-butanol (2EBA). Table VI sets out the data for this control.

TABLE VI

Control - 2-ethyl butanal

| Hours on Stream | % Conversion of 2EBA | % Selectivity to Diene |
|---|---|---|
| 1 | 57 | 68 |
| 2 | 42 | 88 |
| 3 | 39 | 88 |
| 4 | 37 | 83 |
| 5 | 33 | 88 |
| 6 | 31 | 88 |
| 8 | 21 | 89 |
| 10 | 21 | 87 |
| 12 | 20 | 98 |
| 14 | 14 | 99 |
| 16 | 15 | 91 |
| 18 | 15 | 98 |

Experimental 6

The apparatus and procedure as set out above was used except that 2-ethyl-butanol was the feed and catechol at 3% by weight was the aromatic compound for one hour then neat 2-ethylbutanal (2EBA) was used.

TABLE VII

3% Catechol by Weight for 1 hour

| Hours on Stream | | % Conversion of 2EBA | % Selectivity to Diene |
|---|---|---|---|
| 1 | 3% catechol stopped | 15 | 91 |
| 2 | | 24 | 88 |
| 4 | | 33 | 91 |
| 6 | | 37 | 83 |
| 8 | | 37 | 83 |

From this data it is evident that addition of 3% catechol by weight to the 2-EBA feed dramatically improved the catalyst's conversion after 8 hours on stream.

Experimental 7

The procedure and apparatus from Control-II was used except that 3% hydroquinone, aniline, phenol and resorcinol, individually, were added to the 2EBA feed for one hour. Results from each experiment demonstrated a leveling effect on conversion over the control as set out in Table VI.

Experimental—Compounds Outside the Invention

The procedure and apparatus as described above was used except that 2-MBA was the feed and the aromatic compound was selected from the group of: toluene, cumene, cymene, butylated hydroxytoluene and α-methylstyrene. All of these aromatic compounds failed to demonstrate any improvement in catalyst conversions irrespective of % concentration or time on stream.

This data indicates that only specific aromatic compounds have utility in extending the viable lifetime of the dehydration catalyst.

Commercial Utility

This invention will be useful for the production of dienes from aldehydes since it will dramatically lengthen the viable lifetime of the dehydration catalyst.

While certain representative embodiments and details have been shown for the purpose of illustrating the invention, it will be apparent to those skilled in this art that various changes and modifications may be made therein without departing from the spirit or scope of the invention.

I claim:

1. In a process for the conversion of an aldehyde of 4 to 6 carbon atoms to the corresponding diene which comprises contacting the aldehyde in a vapor phase at a temperature of from 200° to 400° C. with a dehydration catalyst, the improvement comprising the addition of from 0.1 to 5.0 percent by weight of an aromatic compound selected from the group consisting of phenol, catechol, alkylated catechol, resorcinol, hydroquinone and aniline; wherein the alkyl radical can be from 1 to 10 carbon atoms; to the aldehyde feed prior to contact with the dehydration catalyst.

2. A process according to claim 1 wherein the dehydration catalyst is boron phosphate and the aldehyde is 2-methylbutanal.

3. A process according to claim 1 wherein the temperature of the reaction is from 275° C. to 350° C.

4. A process according to claim 1 wherein the aromatic compound is 4-t-butyl-catechol.

5. In a process for preparing isoprene which comprises passing 2-methylbutanal in the vapor phase over a boron phosphate dehydration catalyst, the improvement comprising the addition of from 0.1 to 5.0 percent by weight of an aromatic compound selected from the group consisting of phenol, catechol, alkylated catechol, resorcinol, hydroquinone and aniline; wherein the alkyl radical can be from 1 to 10 carbon atoms; to the 2-methylbutanal prior to contact with the catalyst.

6. A process according to claim 5 wherein the temperature of the reaction is from 275° C. to 350° C.

7. A process according to claim 5 wherein the aromatic compound is 4-t-butyl-catechol.

8. In a process for the dehydration of an aldehyde to the corresponding diene, the improvement characterized in that the aldehyde is in physical admixture with from 0.1 to 5.0 weight percent of an aromatic compound selected from the group consisting of phenol, catechol, alkylated catechol, resorcinol, hydroquinone and aniline wherein the alkyl radical can be from 1 to 10 carbon atoms.

9. A process according to claim 8 wherein the temperature of the reaction is from 275° C. to 350° C.

10. A process according to claim 8 wherein the aromatic compound is 4-t-butyl-catechol.

11. A process according to claim 8 wherein the aldehyde is 2-ethylbutanal.

* * * * *